United States Patent [19]

Soothill et al.

[11] 4,210,622

[45] Jul. 1, 1980

[54] KIT FOR ASSAY OF IMMUNE COMPLEXES

[75] Inventors: John F. Soothill; Roland J. Levinsky, both of London, England

[73] Assignee: National Research Development Corporation, London, England

[21] Appl. No.: 926,736

[22] Filed: Jul. 21, 1978

Related U.S. Application Data

[63] Continuation of Ser. No. 831,349, Sep. 7, 1977, Pat. No. 4,141,965.

[51] Int. Cl.² ............................................. G01N 33/16
[52] U.S. Cl. .................................. 422/61; 23/230 B; 23/915; 206/569; 422/57; 424/12
[58] Field of Search ................... 23/230 B; 422/57, 73, 422/61; 424/12

[56] References Cited

U.S. PATENT DOCUMENTS

| 3,826,613 | 7/1974 | Parikh | 424/12 |
| 3,899,298 | 8/1975 | Szezesniak | 23/230 B |
| 4,062,935 | 12/1977 | Masson | 23/230 B |
| 4,092,114 | 5/1978 | Buck | 23/230 B |

FOREIGN PATENT DOCUMENTS 951242  7/1974  Canada.

OTHER PUBLICATIONS

Engvall, J. of Immun., 109(1), 129–135 (1972).

*Primary Examiner*—Sidney Marantz
*Attorney, Agent, or Firm*—Oblon, Fisher, Spivak, McClelland & Maier

[57] ABSTRACT

A method for the estimation of an immune complex and analysis of a constituent thereof, comprising a latex particle agglutination test, in which a sample comprising immune complex is incubated with coated latex particles and IgM antibodies, the latex particles coated with said complex constituent and the IgM antibodies being low affinity non-human antibodies to said complex constituent. There is also provided a kit for use in the method of the invention comprising low affinity non-human IgM antibodies to the constituent of complex undergoing analysis, and latex particles coated with said constituent.

4 Claims, 9 Drawing Figures

KIT FOR ASSAY OF IMMUNE COMPLEXES

This is a continuation of application Ser. No. 831,349, filed Sept. 7, 1977, now U.S. Pat. No. 4,141,965.

This invention relates to the estimation of immune complexes and analysis of constituents thereof.

In recent years immune antigen-antibody complexes have been implicated in the pathogenesis of many human diseases, including systemic lupus erythematosus, rheumatoid arthritis, certain forms of glomerulonephritis and chronic inflammatory bowel diseases. The detection and estimation of immune complexes and their constituents is thus of central importance to the treatment of these diseases; though none of the techniques presently available for their detection and estimation are altogether satisfactory. Physico-chemical techniques generally lack the desired sensitivity; whereas biological methods, though more sensitive, are often highly complex or of only limited applicability and frequently require the use of living cells or human reagents which thus render the methods impractical for wide spread application in hospital laboroatories. For example, a method has been proposed recently (Lurhuma et al (1976) Clin. Exp. Immunol., 25 212) to determine IgG complexes by their inhibition of agglutination, of IgG coated latex particles by rheumatoid factor or Clq. This latter technique is unsatisfactory because of its use of human reagents. Clq and rheumatoid factors, of which rheumatoid factors can be obtained only from ill patients, and also is limited to the detection of the IgG component of IgG complexes.

A simple and effective technique has now been devised for the detection and estimation of immune complexes using characterised non-human reagents and which additionally permits analysis of constituents of the complexes.

Accordingly a method for the estimation of an immune complex and analysis of a constituent thereof comprises a latex particle agglutination test, in which a sample containing immune complex is incubated with coated latex particles and IgM antibodies, the latex particles coated with said complex constituent and the IgM antibodies being low affinity non-human IgM antibodies to said complex constituent.

Any constituent of the immune complex may be analysed by the present method, provided the constituent can be used to produce non-human IgM antibodies and provided the constituent is capable of attachment to latex particles. Thus the antibody constituent e.g. IgM, IgG or IgA, or complement components e.g. $C_3$, of complex may be analysed by the present method. The method may also be employed for analysis of antigen constituents of complex, for instance for analysis of viral, bacterial or other antigenic materials giving rise to complex formation.

Immune complexes are believed to cause disease symptoms, especially tissue damage, and thus the method may be employed either on its own or together with other clinical tests, for diagnosis and monitoring of immune complex associated diseases. For example, the method may be used to monitor the effect of treatment e.g. chemotherapy or plasma-pheresis, upon the levels of immune complex present e.g. in a patient's bloodstream.

The coated latex particles used in the method of the present invention are prepared by linking the complex constituent undergoing analysis to latex particles, and are characteristically in a form suitable for latex particles agglutination tests. Some complex constituents, notably IgG, may undergo spontaneous attachment on contact with latex particles, and, in some cases, coated latex particles may be prepared from such constituents by direct interaction of constituent and latex particles. Other constituents, however, including other immunoglobulin classes, such as IgM and IgA, resist spontaneous attachment and thus it may be desirable to employ a coupling reagent to link some complex constituents to latex particles. Any suitable coupling reagent or activation treatment may be employed.

It has been found, in a preferred embodiment according to the present invention, that dinitrophenol (DNP) is a particularly suitable coupling by which latex particles may be coated with complex constituents. Generally, prior substitution of the complex constituent with DNP permits coating of latex particles with complex constituent which may otherwise resist attachment. Usually 2, 4 dinitrophenol substitution is favoured, though other dinitrophenol substitution may also be employed, and the complex constituent may be DNP substituted by use of any suitable reagent, such as those which are customarily used for DNP substitution. For example, mono-fluoro 2, 4 dinitrobenzene may be used or alternatively the corresponding monochloro or sulphonyl derivatives. It will be appreciated, however, that DNP substitution may be used to couple other biologically active materials to latex particles, besides complex constituents i.e. antibody, antigenic and complement constituents. It will be appreciated also that latex particles coated by DNP linkage, whether with complex constituent or other biologically active material, may be used in other applications besides immune complex assay. For example, latex particles may be coated by the DNP technique with an antigen specific for a particular antibody e.g. a viral antigen, providing a product which agglutinates in the presence of the antibody to that antigen and which may be used as a cheap and simple diagnostic test for the antibody.

Thus in a further aspect the present invention also includes within its scope the use of DNP substitution for coating latex particles with biologically active materials in general, latex particle products coated by the DNP technique and the broad application of these products. Without prejudice it is believed that DNP linkage may be effected by way of tyrosine groups present in the biological material and thus more specifically the DNP technique may potentially be used to link biologically active material, containing tyrosine groups, to latex particles.

The low affinity non-human IgM antibodies used in the immune complex assay method are raised in suitable animals to the constituent of complex which is undergoing analysis. For laboratory purposes small animals such as rabbits and guinea pigs, have been found to be satisfactory for production of these antibodies; however, larger animals such as sheep, cows, or horses may be more desirable for large scale production. Generally, the immune complex constituent, preferably in purified form, is injected into the animal, the animal subsequently bled and low affinity IgM component separated out of the antiserum. Advantageously the yield of low affinity IgM may be optimised having regard to various factors as will be apparent to skilled workers in the art. For instance, the concentration of immune complex constituent injected into the animals, the use of adjuvants, and the site of injection may affect the subsequent yield of antibody. Especially also, the period allowed after injection and before bleeding of the animal may influence the various antibody components present in the antiserum. A period of about ten days has been found to be appropriate for satisfactory low affinity IgM production in rabbits after injection with purified human immunoglobulin classes IgA and IgG in Freund's complete adjuvant. Generally it is also believed that similar periods are appropriate for satisfactory low affinity IgM production with other human immuno-globulins e.g. IgM and IgE.

Characteristically the low affinity non-human IgM antibodies interact specifically with the complex constituent to which they have been raised, and this interaction is typically readily reversable unless the constituent is in an aggregated form e.g. as a component of an immune complex or as a coating on latex particles. Thus on incubation, the IgM antibodies interact strongly, both with latex particles coated with corresponding complex constituent and cause latex particle agglutination, and also with any immune complex, comprising the particular constituent, which is present in the incubate. Thus immune complexes may be estimated and their constituents analysed by the inhibition of agglutination which they cause, the greater the concentration of immune complex the less IgM available for agglutination of the latex particles. For example, sample containing immune complex is mixed with coated latex particles and IgM antibodies, which are preferably in a proportion which in the absence of sample gives a known level of agglutination, and incubated after which the inhibition of agglutination is monitored by a suitable technique.

Generally it is desired to determine immune complexes as a component of a patient's bloodstream, though the present invention may be equally well applied to the determination of immune complexes in other media including other physiological fluids, such as urine. Thus usually samples are derived from serum or other physiological fluid and may desirably undergo suitable preparation before use in the immune complex test. For example, sera is advantageously decomplemented before the test, because free $C_1$ complement components present in the sera may interfere with the assay and give rise to erroneous results. Sera may be decomplemented by heat treatment but this is generally not satisfactory as heat treatment usually also gives rise to unwanted aggregation of protein which may result in false positives in the test. A preferred treatment for decomplementing sera comprises treatment with EDTA to release $C1_q$ which is then removed by an immuno-absorbent, e.g. Sigma-Cell IgG. This preferred decomplementing treatment is also included within the scope of the present invention and is widely applicable to the decomplementing of fluids containing biological material in general.

After decomplementing and/or other preparatory treatment as required, samples e.g. serum samples, are mixed with coated latex particles and low affinity non-human IgM antibodies. The incubate is generally aqueous and incubation is carried out, preferably with agitation, for a period sufficient to complete reaction.

Subsequent to incubation the inhibition of agglutination of latex particles may be monitored by any suitable means. For example, a simple slide agglutination procedure may be employed e.g. relying upon a straightforward visual comparison. Preferably, however, an electronic particle counting apparatus such as a Coulter counter (Coulter Electronics Ltd.), may be used, and for instance may advantageously be programmed to count unagglutinated particles only.

In this latter respect the choice of latex particle size may be important; for instance, it has been found in practice that a latex particle size of diameter about 1.15 $\mu$m is desirable when using a Coulter counter programmed to count unagglutinated particles only. Smaller e.g. less than 0.8 $\mu$m diameter, or larger e.g. greater than 1.5 $\mu$m diameter, particles may be subject to interference by other particles e.g. platelets or aggregates, present in the sample.

The reagents for use in the immune complex assay of the present invention may be supplied to the user in the form of kits and such kits are included within the scope of the invention. For example, a kit for estimation of an immune complex and analysis of a constituent of that complex typically comprises low affinity non-human IgM antibodies to the said constituent of complex, latex particles coated with said constituent, and conveniently also an immuno absorbent e.g. Sigma Cell IgG, and EDTA for decomplementing of the sample. Generally also kits may be supplied for estimation of a range of different types of immune complex and analysis of a range of complex constituents and thus may comprise a corresponding range of low affinity non-human IgM antibodies and coated latex particles. Usually these kits are supplied together with instructions or other indications to enable the user to carry out the immune complex assay of the present invention which advantageously requires little laboratory experience.

The invention is further illustrated in the following non-limiting examples, which refer to the accompanying drawings in which.

EXAMPLE 1—ANTIBODY PRODUCTION

Figure 1:
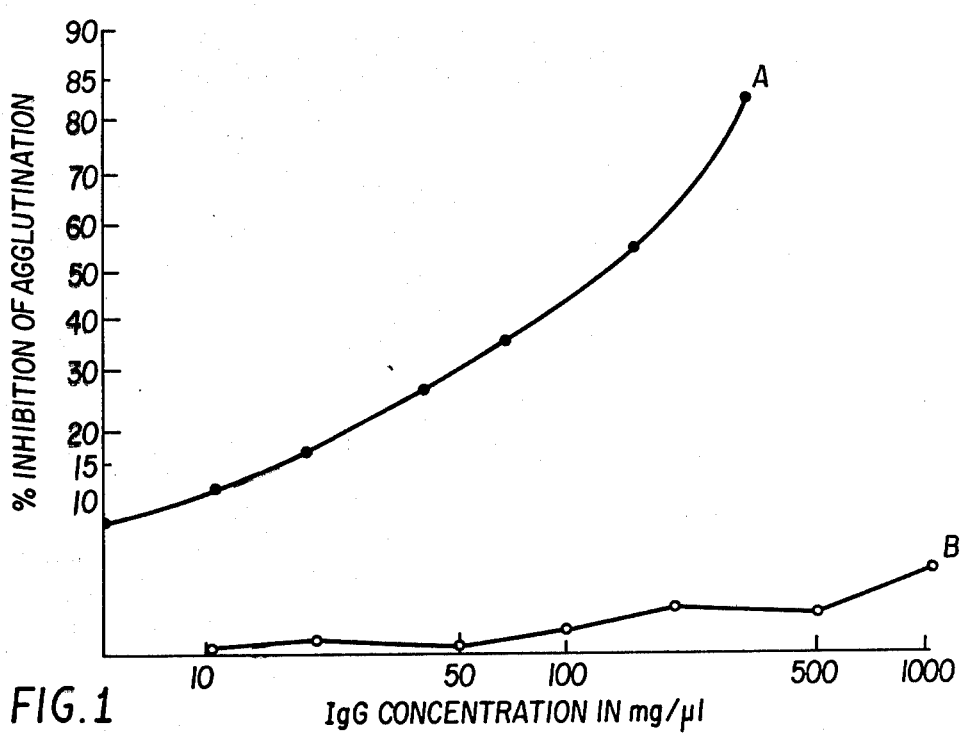
FIG. 1 is a standard curve of inhibition of latex particle agglutination against IgG concentration.

Low affinity IgM antibodies to human immunoglobulin classes IgA, IgM and IgG, for use in the immune complex assay of the present invention, are prepared separately as follows. High purity IgA and IgM are derived from myeloma sera and IgG from pooled fresh frozen plasma by DEAE 52 ion exchange chromatography. 10 mg of each of the purified immunoglobulins in complete Freund's adjuvant is then injected subcutaneously at four different sites into rabbits which are bled 10 days after the first injection.

The sera obtained are separated on a Sephadex G200 column and the IgM peaks collected and concentrated to starting volume by ultrafiltration. Light chain specificity, present in the IgM antisera so produced, is absorbed out by Sepharose (Fab')$_2$ immunosobent columns to give monospecific antisera. The period of ten days between injection and bleeding is found to give reproducible yields of high titre but low affinity IgM antibodies containing no appreciable precipitating or high affinity antibodies.

EXAMPLE 2—COATING OF LATEX PARTICLES

IgA 10 mg of purified human IgA in 1 ml of saline buffer is dialysed for 3 hours at 37° C. against 10% w/v sodium bicarbonate. 3 µl of monofluoro 2, 4 dinitrobenzene is added and the reactants mixed constantly at 37° C. until a bright yellow colour is obtained, at which point the reaction is stopped by adding an equal volume of benzene which extracts excess monofluoro 2, 4 dinitrobenzene. The resultant DNP substituted IgA solution is then purified by dialysis for 24 hours against 1/5 strength 0.27 M glycine saline, pH 8.2.

800 µl of a 10% w/v latex suspension (average particle diameter 1.15 µm) as supplied by Coulter Electronics, is washed twice in 1/5 strength 0.27 M glycine saline pH 8.2. The latex particles are separated from the wash liquid between and after washings by centrifuging at 10,000 r.p.m. and are finally resuspended in 20 ml of the 1/5 strength buffer. 40 µg of the DNP-IgA solution prepared above is then added per mg dry weight of latex and the whole mixed for 30–60 minutes at room temperature. The resultant IgA coated latex product is washed twice with the 1/5 strength buffer and resuspended in 20 ml of full-strength 0.27 M glycine saline buffer containing 0.1% human serum albumin (HSA) which blocks any free reactive sites remaining on the latex particles. The IgA coated latex particle suspension so obtained is suitable for estimation of immune complexes containing an IgA constituent.

Other materials besides IgA which resist spontaneous attachment to latex particles may also be linked by the DNP technique essentially as outlined above, substituting the particular material for IgA in the reaction scheme. Examples of materials which may be linked by the DNP technique include other immunoglobulin classes such as IgM or IgE or other types of materials such as ovalbumin, bovine milk constituents, or soluble viral or bacterial antigens.

Generally also a similar procedure as above is employed for coating of latex particles with materials, such as IgG and HSA, which undergo spontaneous attachment, excepting that DNP activation may be omitted.

EXAMPLE 3—IMMUNE COMPLEX TEST

Sera samples from patients are first decomplemented as follows: 50 µl aliquots of sera are incubated for 10 minutes at room temperature with 50 µl amounts of 0.2 M EDTA pH 7.6 to release C1q. The C1q is then removed from the samples by addition of appropriate amounts of Sigma-cell IgG immuno-absorbent suspended in barbital buffered saline pH 7.4, and subsequent incubation of the samples for a further 20 minutes at room temperature followed by removal of the Sigma-cell IgG by centrifugation. Other methods of decomplementing the sera, including use of similar immuno-absorbents, may be employed, though usually decomplementing by heat treatment is unsatisfactory as aggregation of proteins occurs resulting in false positives in the test.

The low affinity non-human IgM antibody (as prepared in Example 1) is titrated with the corresponding coated latex particles (as prepared in Example 2) e.g. human IgA coated latex particles, and the concentration giving 70% agglutination of the latex is determined. A 100 µl sample of decomplemented test serum diluted 1:10 is mixed with 100 µl of low affinity antibody at appropriate concentration together with 100 µl of coated e.g. IgA coated, latex particles. The whole is then agitated in a plastic tube on a rotating mixer for 30 minutes after which the latex particles are diluted 1:500 in Isoton (Coulter Electronics) and the number of unagglutinated particles counted in a Coulter counter Model ZB, programmed to count single particles only and not aggregates.

The low affinity antibody reacts strongly with both coated latex particles and complex and thus the presence of complex inhibits the agglutination of latex particles.

EXAMPLE 4—PREPARATION OF A STANDARD REFERENCE CURVE

The above immune complex test is carried out using, in place of sera, test solution containing known concentrations of aggregated IgG, and the results obtained are given in the accompanying diagram, FIG. 1. FIG. 1 shows a standard curve A of percentage agglutination (vertical log probit scale) against concentration of aggregated IgG in glycine saline buffer mg/µl (horizontal logarithmic scale) and also includes results obtained in curve B for monomeric IgG showing no appreciable inhibition of agglutination. The standard curve A may be used as a semi-quantitive reference from which immune complex concentrations may be extrapolated from agglutination inhibition results. The log probit scale of the vertical axis of FIG. 1 is a statistically arranged scale which has been used previously for presentation of quantitative haemagglutination results.

EXAMPLE 5

Figure 2:
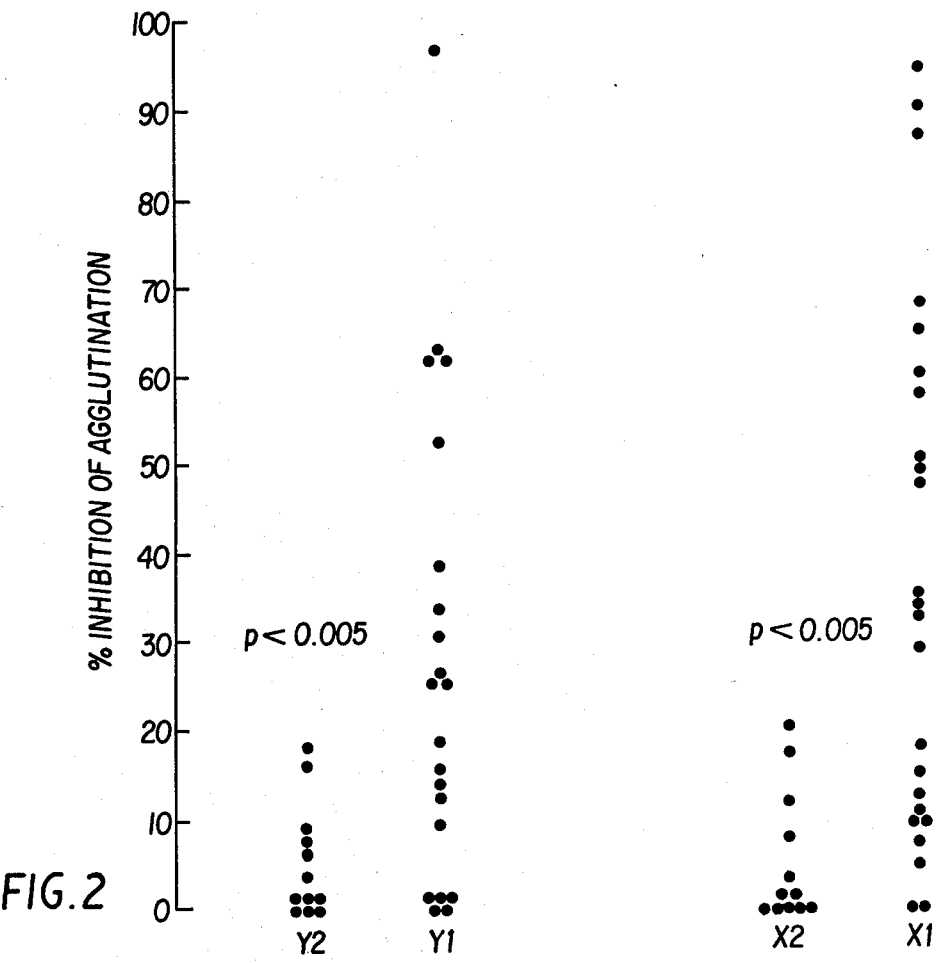
FIG. 2 is a point graph representing the inhibition of latex particle agglutination caused by sera from patients suffering from systemic lupus erythematosus (SLE)
Figure 3A:
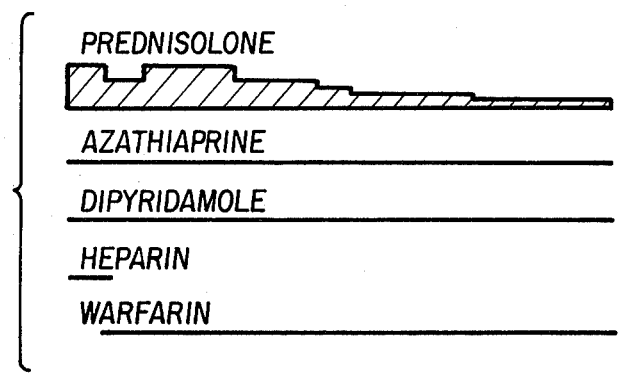
FIG. 3 is a series of graphs representing the clinical history of a patient suffering from lupus nephritis and FIG. 4 is a graphical representation of the IgA and IgG complex activities of separated fractions of serum from a patient suffering from Henoch-Schonlein purpura nephritis.
Figure 3B:
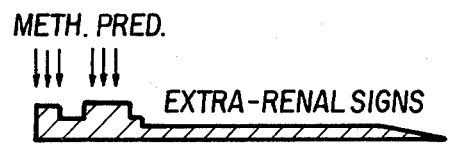
Figure 3C:
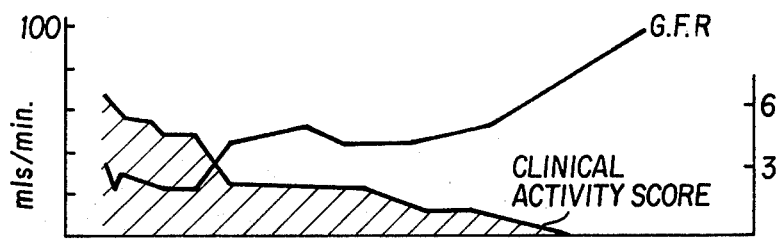
Figure 3D:
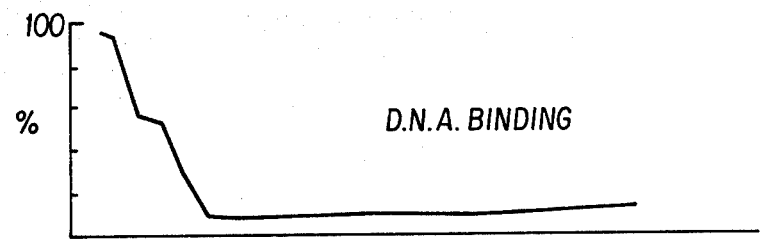
Figure 3E:
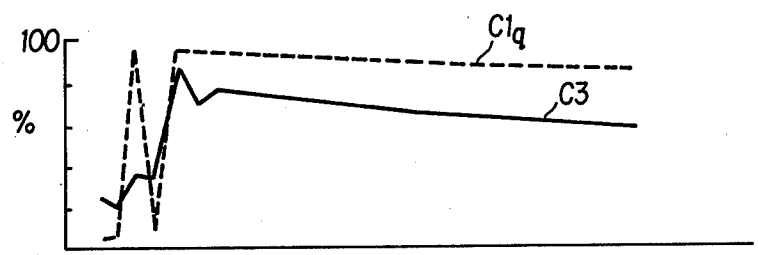
Figure 3F:
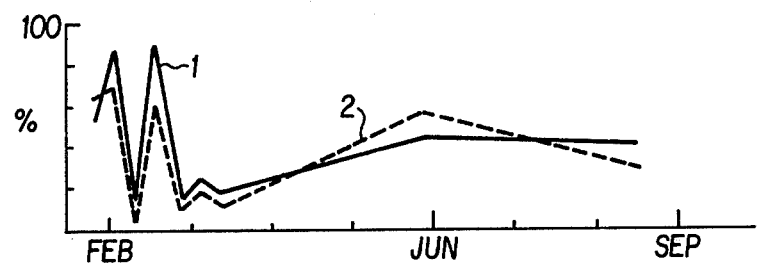

The immune complex test of Example 3 for determination of IgG complexes is applied to the decomplemented sera of 24 patients suffering from systemic lupus erythematosus (SLE) using low affinity rabbit IgM anti-human IgG antibodies and IgG coated latex particles. The results obtained are given in column X1 of FIG. 2 showing the percentage inhibition of agglutination for each patient, column X2 giving corresponding results for 12 control sera. For comparison the sera of 21 of the original group of SLE patients is also tested by the C1q latex particle agglutination technique described by Lurhuma et al (Clin. Exp. Immunol. 25, 212 (1976) adapted by use of a Coulter counter as in the technique of Example 3. The results obtained for the C1q test are given in column Y1 of FIG. 2, together with corresponding control results in column Y2, and clearly show good agreement between the test of the present invention and the adapted Lurhuma test.

EXAMPLE 6

The immune complex test of Example 3, for determination of IgG complexes, is used to monitor the course of an 18 year old woman who presented with lupus nephritis soon after delivery of her first child. The results obtained are given in line 1 FIG. 3 (f) together with results obtained, in line 2, using the modified Lurhuma test as in previous examples. The patient initially suffered renal failure, rash, fever, myocarditis and convulsions; DNA binding was high, serum $C_3$, $C_4$ and C1q levels were reduced, and renal biopsy showed severe diffuse proliferative glomerulonephritis. The patient was treated with azathioprine, prednisolone, dipyridamole, anticoagulants and methyl prednisolone pulse therapy (1 gm/day i/v for 3 days). FIG. 3 also includes information concerning medication (3a), methyl prednisolone therapy and extra renal signs (3b), GFR and clinical activity (3c), DNA binding (3d) and serum C1q and C3 complement levels (3e) throughout the course of the illness.

With reference to FIG. 3 serum immune complex levels were initially very high and fell dramatically after methyl prednisolone therapy which corresponded with an improvement in the patient's condition. The serum complex levels, however, again rose giving an early warning signal of the patient's relapse, on the following day, with myocarditis and convulsions. The patient was again subjected to methyl prednisolone therapy, improved, and serum complex levels fell again. The transient rise in the levels of immune complexes in June were associated with a minor relapse of fever and rash.

This example clearly shows how the test of the invention assists in the monitoring of an immune complex associated illness.

EXAMPLE 7

2 ml of serum from an 11 year old boy suffering from Henoch-Schonlein purpura nephritis is separated on a calibrated Sepharose C.L. 68 column (90×3.2 cm), and all fractions obtained are tested for IgA and IgG complexes by the immune complext test substantially as in Example 3. IgA complexes are estimated by their inhibition of agglutination of IgA latex, by rabbit IgM antihyman IgA, and IgG complexes by their inhibition of agglutination of IgG latex, by rabbit IgM anti-human IgG. The results obtained are given in FIG. 4 which is in the form of a plot Y of the elution pattern of the factions in terms of optical density at 280 nm (left hand y axis o.d.), together with vertical lines corresponding to the magnitude of inhibition (right hand y axis % inhibition). Only results showing greater than 3% inhibition are plotted.

Figure 4:
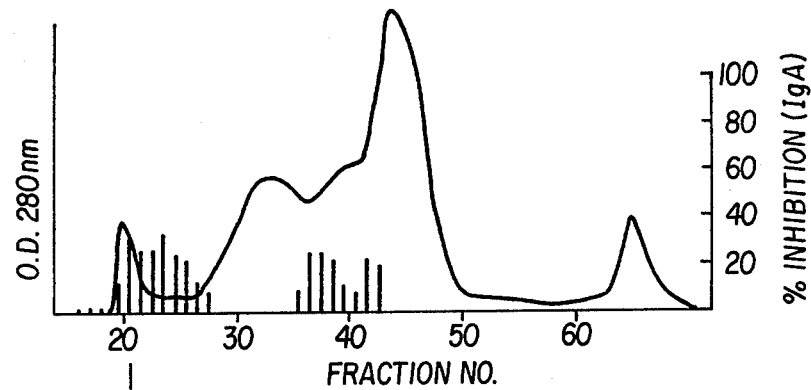

FIG. 4 shows that the serum contains two populations of IgA containing complexes corresponding to the $2.5-4 \times 10^6$ and $4-8 \times 10^5$ molecular weight ranges, and also a small amount of IgG containing complexes in the $3.5-4 \times 10^6$ m.w. range.

We claim:

1. A kit for use in the estimation of a human immune complex and analysis of a constituent thereof by a latex particle agglutination test comprising a carrier with
   a first vial which contains low affinity non-human IgM antibodies raised in a non-human animal against the constituent of said human complex undergoing analyses; and
   a second vial containing latex particles sufficiently coated with said constituent, so that said latex particles may be agglutinated when said particles are mixed with said IgM antibodies of the first vial.

2. A kit according to claim 1 comprising in addition, a third vial containing EDTA and an immuno-absorbent for decomplementing the sample.

3. A kit according to claim 1, wherein a range of low affinity non-human IgM antibodies and a range of coated latex particles is contained in various vials for estimation of a corresponding range of immune complexes and analysis of a range of complex constituents.

4. A kit according to claim 1 wherein said constituent is linked to said latex particles by means of a DNP linking group.

* * * * *